US009737259B2

United States Patent
Hong et al.

(10) Patent No.: US 9,737,259 B2
(45) Date of Patent: Aug. 22, 2017

(54) SYSTEM AND METHOD FOR DETERMINING NEOINTIMA THICKNESS OF A BLOOD VESSEL

(71) Applicants: Industry-Academic Cooperation Foundation, Yonsei University, Seoul (KR); Industry-Academia Cooperation Group of Sejong University, Seoul (KR)

(72) Inventors: Myeong Ki Hong, Seoul (KR); Byeong Keuk Kim, Seoul (KR); Jin Yong Ha, Seoul (KR)

(73) Assignees: Industry-Academic Cooperation Foundation, Yonsei University, Seoul (KR); Industry-Academia Cooperation Group of Sejong University, Seoul (KR)

(*) Notice: Subject to any disclaimer, the term of this patent is extended or adjusted under 35 U.S.C. 154(b) by 1184 days.

(21) Appl. No.: 13/851,198

(22) Filed: Mar. 27, 2013

(65) Prior Publication Data
US 2014/0296703 A1  Oct. 2, 2014

(51) Int. Cl.
*A61B 5/00* (2006.01)
*A61B 6/00* (2006.01)
(Continued)

(52) U.S. Cl.
CPC .......... *A61B 5/4851* (2013.01); *A61B 5/0066* (2013.01); *A61B 5/1076* (2013.01);
(Continued)

(58) Field of Classification Search
None
See application file for complete search history.

(56) References Cited

U.S. PATENT DOCUMENTS

2010/0094127 A1* 4/2010 Xu ............ A61B 5/0066
600/425

FOREIGN PATENT DOCUMENTS

JP  2001520057 A  10/2001
JP  2003284719 A   7/2003
(Continued)

OTHER PUBLICATIONS

Chico et al, Tissue coverage of a hydrophilic polymer-coated zotarolimus-eluting stent vs. a fluoropolymercoated everolimus-eluting stent . . . European Heart Journal, 2011, 32, 2454-2463.*
(Continued)

*Primary Examiner* — Serkan Akar
(74) *Attorney, Agent, or Firm* — Hammer & Associates, P.C.

(57) ABSTRACT

A system and method for providing an image capable of realizing conversion of a 3D tissue structure into which an implant is inserted into a 2D image using a contour technique are provided. The system for providing an image includes an imaging unit configured to photograph an inner part of a blood vessel into which an implant is inserted to provide a plurality of tomographic images, a first analysis unit configured to analyze the plurality of tomographic images to generate data on strut distribution of the stent, a second analysis unit configured to analyze the plurality of tomographic images to generate data on a thickness of a neointima, a first image generation unit configured to generate a strut distribution chart of a 2D image using the data on the strut distribution, a second image generation unit configured to generate a contour map for the thickness of the neointima using the data on the thickness of the neointima, and a composition unit configured to composite the strut distribution chart and the contour map.

10 Claims, 7 Drawing Sheets

(51) Int. Cl.
- *A61B 8/08* (2006.01)
- *A61B 5/107* (2006.01)
- *A61B 8/12* (2006.01)
- *A61B 6/03* (2006.01)
- *A61B 6/12* (2006.01)

(52) U.S. Cl.
CPC ................ *A61B 6/032* (2013.01); *A61B 6/12* (2013.01); *A61B 6/463* (2013.01); *A61B 6/504* (2013.01); *A61B 6/5223* (2013.01); *A61B 8/0841* (2013.01); *A61B 8/12* (2013.01)

(56) References Cited

FOREIGN PATENT DOCUMENTS

| | | |
|---|---|---|
| KR | 1020100139049 A | 12/2010 |
| WO | WO 2010/045386 A1 | 4/2010 |

OTHER PUBLICATIONS

Raber et al, Long-Term Vascular Healing in Response to Sirolimus- and Paclitaxel-Eluting Stents, JACC: Cardiovascular Interventions vol. 5, No. 9, 2012.*

Byeong-Keuk Kim et al., "A New Method for Assessing Neointimal Coverage After Drug-Eluting Stent Implantation Using Three-Dimensional Optical Coherence Tomography," JACC Journals, (vol. 59), (Issue. 13), (Mar. 27, 2012).

* cited by examiner

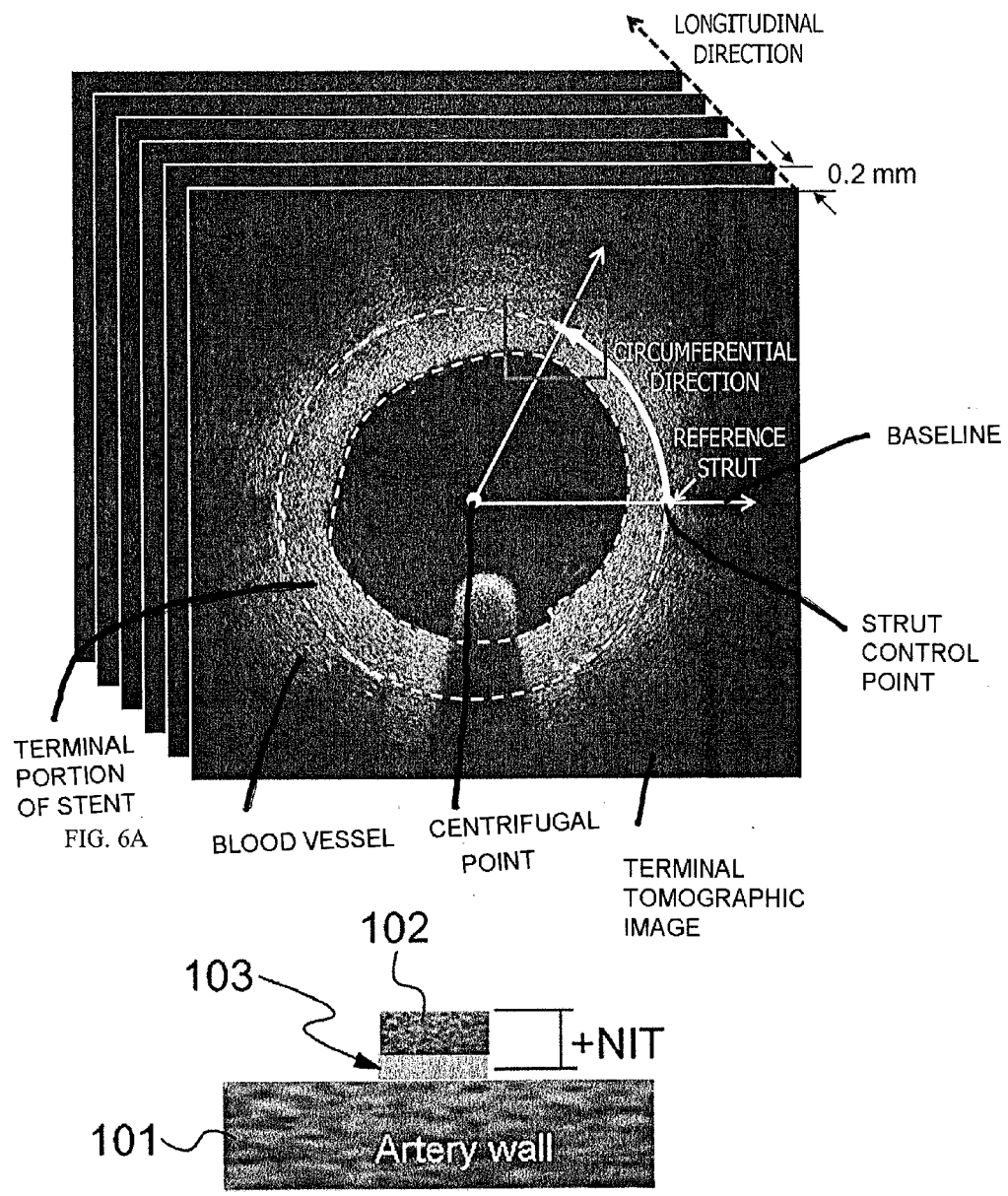

Strut Distribution Chart

Composite Strut Distribution Chart
and/or
Contour Map

SYSTEM AND METHOD FOR DETERMINING NEOINTIMA THICKNESS OF A BLOOD VESSEL

BACKGROUND

1. Field of the Invention

The present invention relates to a system and method for providing an image capable of generating an image providing information on an implant distributed in a tissue into which the implant is inserted and binding between the implant and the tissue.

2. Discussion of Related Art

Major causes of failure in implant placement are mainly divided into problems associated with implant materials caused during the implant placement, such as poor initial contact between a bone and a surface of an implant and peeling of a coated surface layer, and problems caused after the implant placement, such as an in vivo rejection response caused by reactive oxygen and various oxidants accumulated in osteocytes, stress, the onset of periimplantitis. This is because an implant and an osseous tissue surrounding the implant, both of which have different physical properties, are structurally brought into contact with each other to form an interface therebetween, and thus a biological tissue and an osteocyte (i.e., a bone cell) are not integrated to a surface of an artificial implant (osseointegration). Therefore, when the implant is placed in a tissue, stenosis or osseointegration of the implant should be easily observed.

Also, when a stent is inserted into a blood vessel during cardiovascular intervention, it is important to determine the onset of stenosis of a stent in an outer wall of a blood vessel. After the cardiovascular intervention, optical coherence tomography (OCT) using a laser is used to determine whether the stent is stenosed in the blood vessel. Also, neointimal cells grow on the strut after the cardiovascular intervention. In this case, the blood vessel narrows again due to the overgrowth of intimal cells. Therefore, various clinical results obtained according to a condition of a patient, a structure of a stent, and drug ingredients presented to a surface of the stent are read from an OCT image. To analyze the clinical results, a thickness of a neointima after growth of intimal cells on the strut is measured from a sectional image of a blood vessel and quantified using statistical analysis.

However, the statistical analysis has a limit in qualitative analysis since it is merely quantitative analysis. For example, the thickness and presence of the neointima are expected to vary according to a drug presented to the stent. To analyze the analysis results, a structure and location of the stent in the blood vessel should be analyzed on a structure of the blood vessel other than a section of the blood vessel.

SUMMARY OF THE INVENTION

The present invention is directed to providing a system and method for providing an image capable of realizing conversion of a three-dimensional (3D) tissue structure into which an implant is inserted into a two-dimensional (2D) image using a contour technique.

The present invention is also directed to providing a system and method for providing an image capable of generating an image including information on a location of an implant in a tissue, distribution, periimplantitis, a state of stenosis, and a thickness of a neointima.

One aspect of the present invention provides a system for providing an image, which includes an imaging unit configured to photograph a tissue into which an implant is inserted to provide a plurality of tomographic images, a first analysis unit configured to analyze the plurality of tomographic images to generate information on a location of the implant, a second analysis unit configured to analyze the plurality of tomographic images to generate information on binding between the implant and the tissue, a first image generation unit configured to generate an implant location information map of a 2D image using the information on the location of the implant, a second image generation unit configured to generate a contour map for the information on binding between the implant and the tissue using the information on binding between the implant and the tissue, and a composition unit configured to composite the implant location information map and the contour map.

The implant may be one selected from the group consisting of a stent, a pin, a screw, a plate, a mesh structure, an orthopedic device, an RFID tag, a pacemaker (i.e., an artificial pacemaker), a gastric band, and an esthetic implant.

The implant location information map may be represented by a coordinate of the implant in a longitudinal direction and a coordinate of the implant in a circumferential direction.

The information on binding between the implant and the tissue may include periimplantitis, a state of stenosis, or a thickness of a neointima.

The composition unit may be configured to composite the implant location information map and the contour map on the same coordinate.

The system for providing an image according to the present invention may further include a display unit configured to externally display the image composited at the composition unit.

Another aspect of the present invention provides a system for providing an image, which includes an imaging unit configured to photograph an inner part of a blood vessel into which a stent is inserted to provide a plurality of tomographic images, a first analysis unit configured to analyze the plurality of tomographic images to generate data on strut distribution of the stent, a second analysis unit configured to analyze the plurality of tomographic images to generate data on a thickness of a neointima, a first image generation unit configured to generate a strut distribution chart of a 2D image using the data on the strut distribution, a second image generation unit configured to generate a contour map for the thickness of the neointima using the data on the thickness of the neointima, and a composition unit configured to composite the strut distribution chart and the contour map.

The first analysis unit may be configured to generate the data on the strut distribution by measuring a strut location of the stent in a blood vessel in a longitudinal direction and a strut location of the stent in a circumferential direction.

The first analysis unit may be configured to measure a strut location of the stent in a longitudinal direction with respect to a terminal portion of the stent, and measure a strut location of the stent in a circumferential direction with respect to a strut control point colliding with a baseline extending from a centrifugal point of the stent.

The first image generation unit may be configured to generate the strut distribution chart using the x axis of the 2D image as the strut location of the stent in a circumferential direction and the y axis of the 2D image as the strut location of the stent in a longitudinal direction.

The second analysis unit may be configured to generate the data on the thickness of the neointima using a difference between a linear distance running from the strut to an outer wall of a new blood vessel and a linear distance running from a preexisting vessel wall to the strut.

The second image generation unit may be configured to draw a contour line by connecting points having the same difference and generate the contour map using the contour line.

The system for providing an image according to the present invention may further include a third analysis unit configured to analyze the plurality of tomographic images and generate data on strut stenosis according to a state of stenosis of the strut in the blood vessel. Here, the first image generation unit may be configured to discriminatively display struts on the strut distribution chart according to the data on the strut stenosis.

The imaging unit may be configured to photograph the plurality of tomographic images in a longitudinal direction of the blood vessel at intervals of 0.06 to 0.2 mm so as to provide the plurality of tomographic images.

The composition unit may be configured to composite the strut distribution chart and the contour map on the same coordinate.

The system for providing an image according to the present invention may further include a display unit configured to externally display the image composited at the composition unit.

The display unit may be configured to externally display a tomographic image including struts on the image composited at the composition unit.

The display unit may be configured to discernibly display the struts on the tomographic image.

Still another aspect of the present invention provides a method of providing an image. Here, the method includes photographing a tissue into which an implant is inserted to provide a plurality of tomographic images at an imaging unit, analyzing the plurality of tomographic images to generate information on a location of the implant at a first analysis unit, analyzing the plurality of tomographic images to generate information on binding between the implant and the tissue at a second analysis unit, generating an implant location information map of a 2D image at a first image generation unit using the information on the location of the implant, generating a contour map for the information on binding between the implant and the tissue at a second image generation unit using the information on binding between the implant and the tissue, compositing the strut distribution chart and the contour map at a composition unit, and externally displaying the image composited at the composition unit at a display unit.

The generation of the implant location information map may include generating the implant location information map by measuring a location of the implant in a tissue in a longitudinal direction and a location of the implant in a circumferential direction.

The generation of the contour map may include drawing a contour line by connecting points having the same values for the information on binding between the implant and the tissue on the 2D image, and generating the contour map using the contour line.

The photographing of the tissue may include photographing the plurality of tomographic images in a longitudinal direction of the blood vessel at intervals of 0.2 mm or less so as to provide the plurality of tomographic images.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which:

FIG. 5 is a diagram showing a plurality of tomographic images photographed at an imaging unit according to one exemplary embodiment of the present invention;

FIG. 6A-D are diagrams showing the shapes of neointimas grown according to a state of a strut which is stenosed in a vessel wall;

DETAILED DESCRIPTION OF EXEMPLARY EMBODIMENTS

Figure 1:
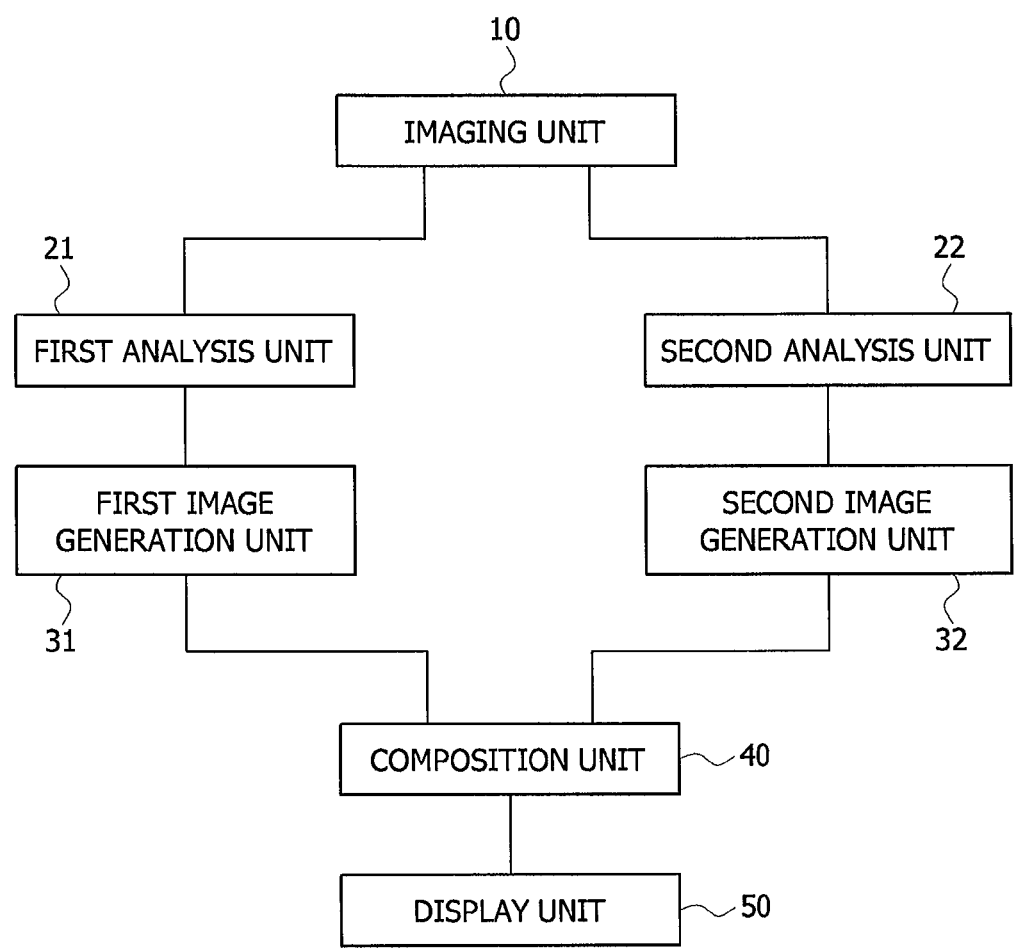
FIG. 1 is a block diagram showing a system for providing an image according to one exemplary embodiment of the present invention.

Hereinafter, exemplary embodiments of the present invention will be described in detail. However, the present invention is not limited to the embodiments disclosed below but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

As used in the present invention, the term "implant" refers to a stent, a pin, a screw, a plate, a mesh structure, an orthopedic device, an RFID tag, a pacemaker (i.e., an artificial pacemaker), a gastric band/collar, an esthetic implant, or another device suitable for being transplanted into a mammal subject. An exemplary implant is a device that can radially expand to be introduced into a subject, such as an expandable blood vessel stent.

Also, the term "tissue" refers to a body tissue in which an implant can be placed, such as a bone, a tooth, a blood vessel, etc.

Information on binding between the implant and the tissue used in the present invention includes all kinds of information that can be obtained between an external surface of an implant and a tissue into which the implant is inserted, for example, a progression level of periimplantitis, a state of stenosis formed between the external surface of the implant and the tissue, or a thickness of a neointima.

FIG. 1 is a block diagram showing a system for providing an image according to one exemplary embodiment of the present invention. The system for providing an image according to one exemplary embodiment of the present invention includes an imaging unit 10, a first analysis unit 21, a second analysis unit 22, a first image generation unit 31, a second image generation unit 32, a composition unit 40, and a display unit 50.

Figure 4:
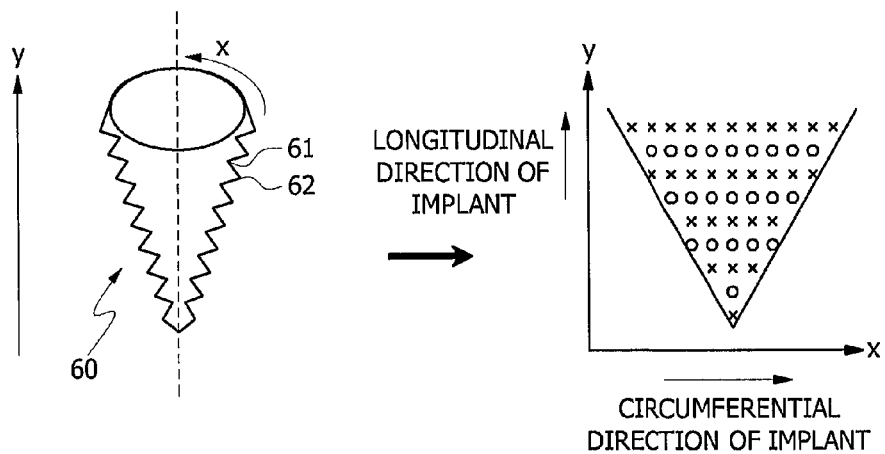
FIG. 4 is a concept diagram of a method of providing an image according to one exemplary embodiment of the present invention.

The imaging unit 10 serves to photograph a tissue into which an implant is inserted to provide a plurality of tomographic images of the tissue. A computed tomography (CT) device is known as the imaging unit 10 capable of providing a plurality of tomographic images. For example, to provide a tomographic image in a blood vessel, an intravascular ultrasound (IVUS) or optical coherence tomography (OCT) technique may be used. The intravascular ultrasound technique is used to apply ultrasound with 40 MHz exceeding an audible frequency of 20 kHz to a cellular tissue, convert the ultrasound reflected on the cellular tissue into an image to analyze the cellular tissue, and provide various kinds of direct and detailed information on changes in a blood vessel lumen, atherosclerotic plaque, and a vessel wall. Like the ultrasound technique, the OCT technique is also a medical imaging technique configured to apply light derived from a laser to a cellular tissue and convert the light reflected on the cellular tissue into an image. The OCT technique has a resolution of approximately 15 μm, and thus provides a high-resolution section image on whether a stent strut having a thickness of approximately 100 μm is sufficiently stenosed in a blood vessel. The imaging unit 10 is inserted into a blood vessel to photograph a plurality of tomographic images while moving in a longitudinal direction of the blood vessel using a monorail technique. The imaging unit 10 may provide the plurality of tomographic images photographed at intervals of, for example, 0.06 to 0.2 mm while moving in a longitudinal direction of the blood vessel using the monorail technique The first analysis unit 21 may analyze the plurality of tomographic images photographed at the imaging unit 10 to generate information on a location of the implant. FIG. 4 shows a location information map of the implant according to one exemplary embodiment of the present invention. The information on the location of the implant refers to information obtained by representing a 3D implant structure of the implant using a coordinate of the implant in a longitudinal direction and a coordinate of the implant in a circumferential direction. Referring to FIG. 4, when the implant 60 has a thread shape, a surface of the implant 60 has an uneven structure including valleys 61 and peaks 62. A 3D shape of the implant may be displayed in the form of a 2D implant by severing the implant 60 in a longitudinal direction, presenting the x axis and the y axis in a circumferential direction and a longitudinal direction, respectively, and displaying the valleys 61 and the peaks 62 using different symbols, for example, O and X, on a development figure.

According to another exemplary embodiment, when the implant is a stent having a strut inserted into a blood vessel, the information on the location of the implant may mean data on strut distribution of the stent. The data on strut distribution may mean location coordinates of a plurality of stent struts in a blood vessel, that is, 2D coordinates in a plurality of tomographic images. The first analysis unit 21 may generate the data on strut distribution into the 2D coordinates by measuring a strut location of the stent in a longitudinal direction and a strut location of the stent in a circumferential direction. To provide a 2D image for the data on strut distribution, the first analysis unit 21 may measure the strut location of the stent in a longitudinal direction with respect to a terminal portion of the stent, and measure the strut location of the stent in a circumferential direction with respect to a strut control point colliding with a baseline extending from a centrifugal point of the stent. When the first tomographic image shown in FIG. 5 is a tomographic image of a terminal portion of the stent inserted into a blood vessel, data on strut distribution composed only of 2D coordinates may be generated by measuring a strut stenosis location at a tomographic image interval of 0.2 mm in a longitudinal direction with respect to the first tomographic image, and measuring an arc length running from a baseline extending from a centrifugal point of the stent and a strut control point, which collides with a circular arc connecting struts, to each strut in a circumferential direction. The strut control point is used to determine locations of struts in a circumferential direction of the stent. As shown in FIG. 5, the strut control point is a point colliding with a circular arc connecting struts when a horizontal line, that is, a baseline, extends from a centrifugal point of the stent.

Figure 7:
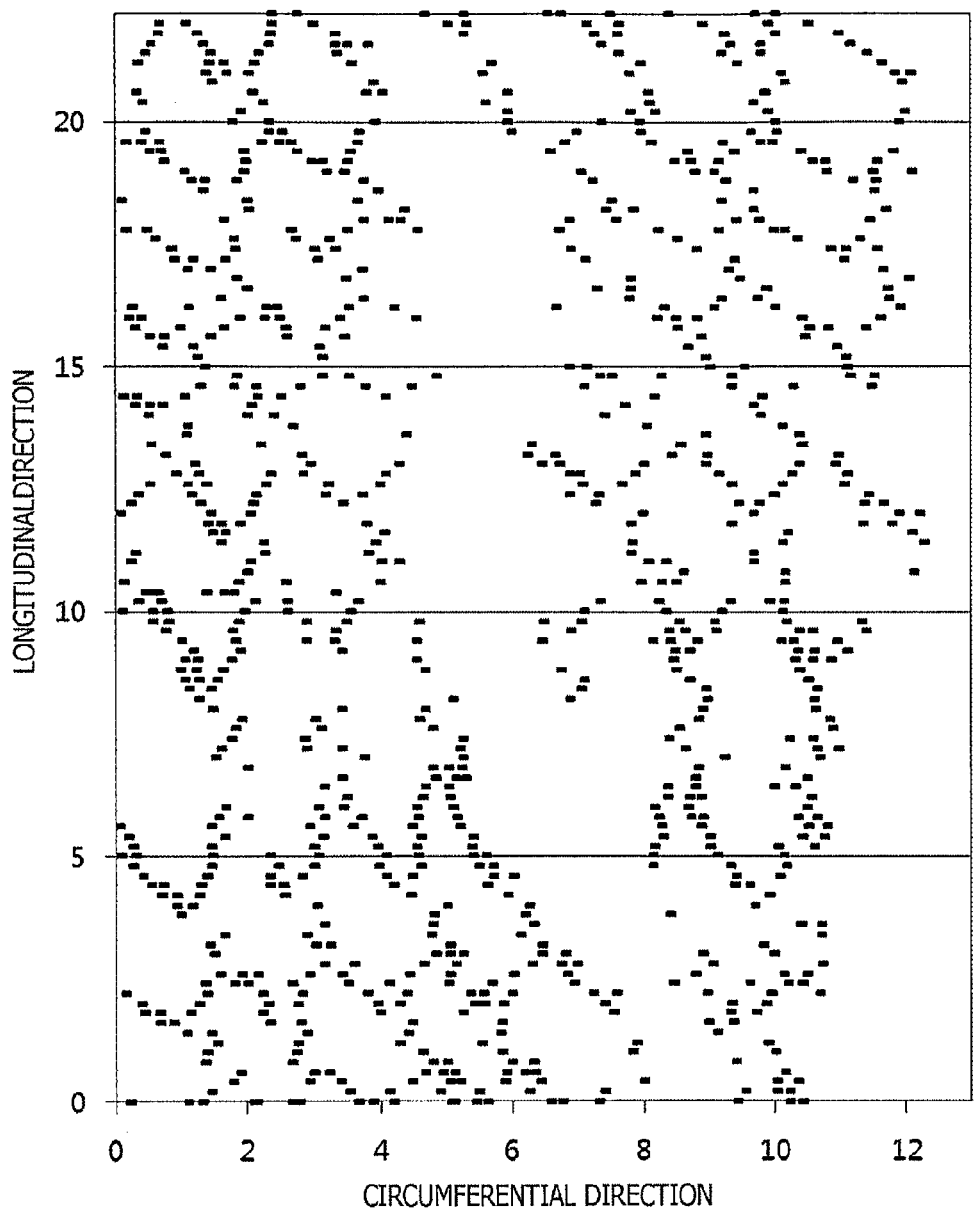
FIG. 7 is a diagram showing a strut distribution chart generated at a first analysis unit according to one exemplary embodiment of the present invention.

The first image generation unit 31 may generate a strut distribution chart of a 2D image using the data on strut distribution. The strut distribution chart shows locations of the struts distributed in a blood vessel on the 2D image. When the blood vessel into which the stent is inserted is severed and spreads in a longitudinal direction, the strut distribution chart means a pattern in which the struts are distributed on the unfolded blood vessel. The first image generation unit 31 may use the data on strut distribution of the 2D coordinates generated at the first analysis unit 21 to generate the strut distribution chart in which the x axis and the y axis are used as a strut stenosis location of the stent in a circumferential direction and a strut stenosis location of the stent in a longitudinal direction, respectively. On the contrary, the first image generation unit 31 may also generate a strut distribution chart in which the x axis and the y axis are changed in location. The strut distribution chart may be generated as shown in FIG. 7.

Figure 6B:
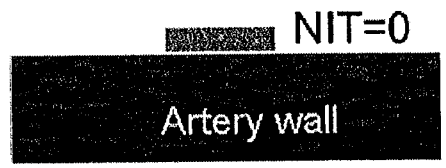
Figure 6C:
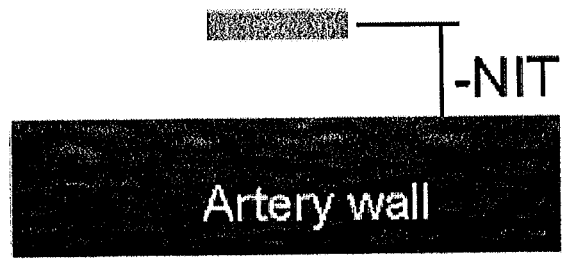
Figure 6D:
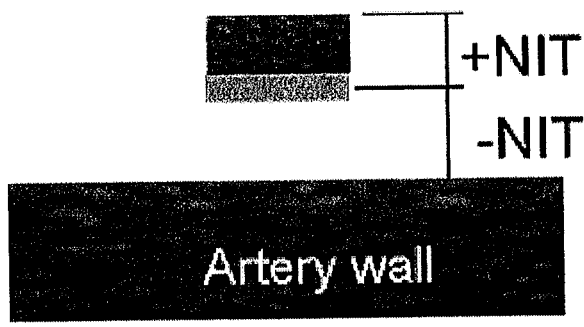

The second analysis unit 22 may analyze the plurality of tomographic images photographed at the imaging unit 10 to generate information on binding between the implant and the tissue. When the information on binding between the implant and the tissue is data on a thickness of a neointima, the data on the thickness of the neointima means a height running from a blood vessel strut to a newly formed vessel wall. Since the strut is surrounded by the neointima formed after stenosis of the strut, a linear distance running from the strut to the newly formed vessel wall becomes a thickness of the neointima. However, even when the strut is not stenosed in a vessel wall since it is located in a wrong place of the blood vessel, the strut is surrounded by the neointima formed around the vessel wall. In this case, a thickness of the neointima may be a value obtained by subtracting a linear distance running from a preexisting vessel wall to the strut from a linear distance running from the strut to a vessel wall. That is, when the strut 103 is stenosed in a vessel wall as shown in FIG. 6A, a linear distance running from the strut to a newly formed vessel wall 102 becomes a thickness (NIT) of the neointima. However, when the strut 103 is not stenosed in a preexisting vessel wall 101 as shown in FIG. 6D, a value, which is obtained by subtracting a linear distance running from the preexisting vessel wall 101 to the strut 103 from a linear distance running from the strut 103 to the newly formed vessel wall 102, becomes a thickness of the neointima. Also, when the strut 103 is stenosed in a vessel wall but the neointima is not generated as shown in FIG. 6B, a thickness of the neointima becomes zero (0). Also, when the neointima is not generated in a state in which the strut 103 is not stenosed in a vessel wall as shown in FIG. 6C, a thickness of the neointima becomes a negative number having a size corresponding to a linear distance running from the preexisting vessel wall 101 to the strut 103. A distance running from the strut to the neointima or vessel wall may be measured from the center of the strut, or measured from an upper/lower end of the strut, as shown in FIGS. 6A to 6D.

The second image generation unit 32 may generate a contour map for the information on binding between the implant and the tissue generated at the second analysis unit 22 using the information on binding between the implant and the tissue. For example, the contour map for a thickness of the neointima refers to a contour map in which a thickness of the neointima formed in a preexisting vessel wall after insertion of the stent is a height of a contour line. The second image generation unit 32 may draw a contour line by connecting points having the same values obtained from the data of the thickness of the neointima generated at the second analysis unit 22, and generate a contour map using the contour line.

The composition unit 40 may generate an image obtained by compositing the implant location information map generated at the first image generation unit 31 and the contour map generated at the second image generation unit 32. The composition unit 40 may composite the strut distribution chart and the contour map on the same coordinates using an image or an image composition technique generally used in the related art, for example, using a blending technique through a pixel operation.

The display unit 50 may serve to externally display the image composited at the composition unit 40. Also, the display unit 50 may externally display a tomographic image including struts on the image composited at the composition unit. In this case, light, shade, a shape, or a color may be used to display the tomographic image so that some struts can be discerned from the other struts. For example, when information on any struts formed on the contour image composited at the composition unit and displayed at the display unit is required, any struts may be selected to provide a tomographic image. Any struts on the contour image may be selected through external input, and a tomo-graphic image of the struts corresponding to a preset condition, for example, the struts which is not stenosed in a vessel wall, may be automatically connected to be externally displayed. The display unit 50 means a conventional display device configured to visually output data on a screen, such as CRT, LCD, PDP, LED, or OLED.

Figure 2:
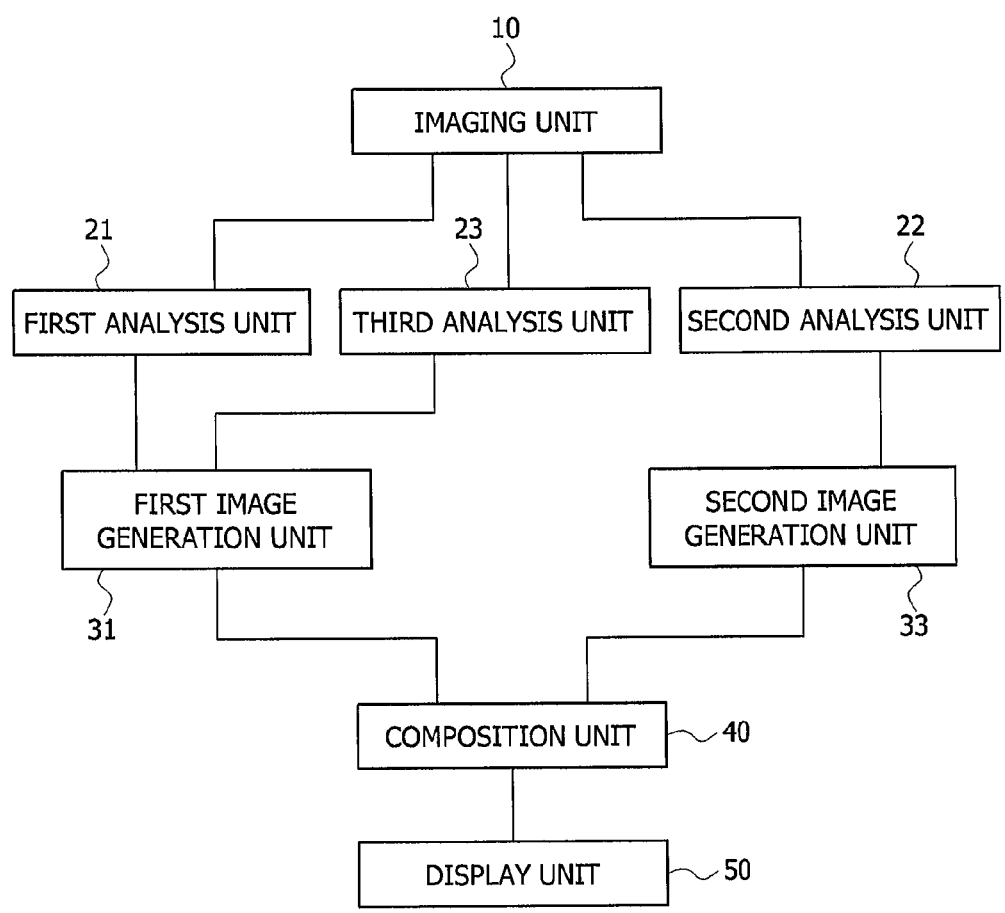
FIG. 2 is a block diagram showing a system for providing an image according to another exemplary embodiment of the present invention.

FIG. 2 is a block diagram of a system for providing an image according to another exemplary embodiment of the present invention. The system for providing an image shown in FIG. 2 has the same configuration as in FIG. 1 except for the third analysis unit 23 and the first image generation unit 31, and thus description of the same parts is omitted for clarity.

The third analysis unit 23 analyzes the plurality of tomographic images photographed at the imaging unit 10 to generate additional information on binding between the implant and the tissue, which is not analyzed at the second analysis unit 22. For example, when a progression level of periimplantitis is analyzed at the second analysis unit 22, the third analysis unit 23 may generate data on stenosis indicating a progression level of the stenosis of the implant in the tissue. Also, when the data on the thickness of the neointima is analyzed at the second analysis unit 22, the third analysis unit 23 may generate data on strut stenosis according to a state of stenosis of the strut in the blood vessel. The data on strut stenosis refers to classification data on whether a strut is stenosed in a vessel wall, for example, data classified into a case in which the strut is stenosed in a vessel wall and surrounded by the neointima, a case in which the strut is stenosed in the vessel wall but is not surrounded by the neointima (uncovered in FIG. 8), and a case in which the strut is not stenosed in the vessel wall (malapposed in FIG. 8). Also, the data on strut stenosis may be data according to fours states of strut stenosis, as shown in FIG. 6.

The first image generation unit 31 may use the data on strut stenosis generated at the third analysis unit 23 to display the struts shown on the strut distribution chart in different colors or shapes, depending on each state of strut stenosis.

Figure 8:
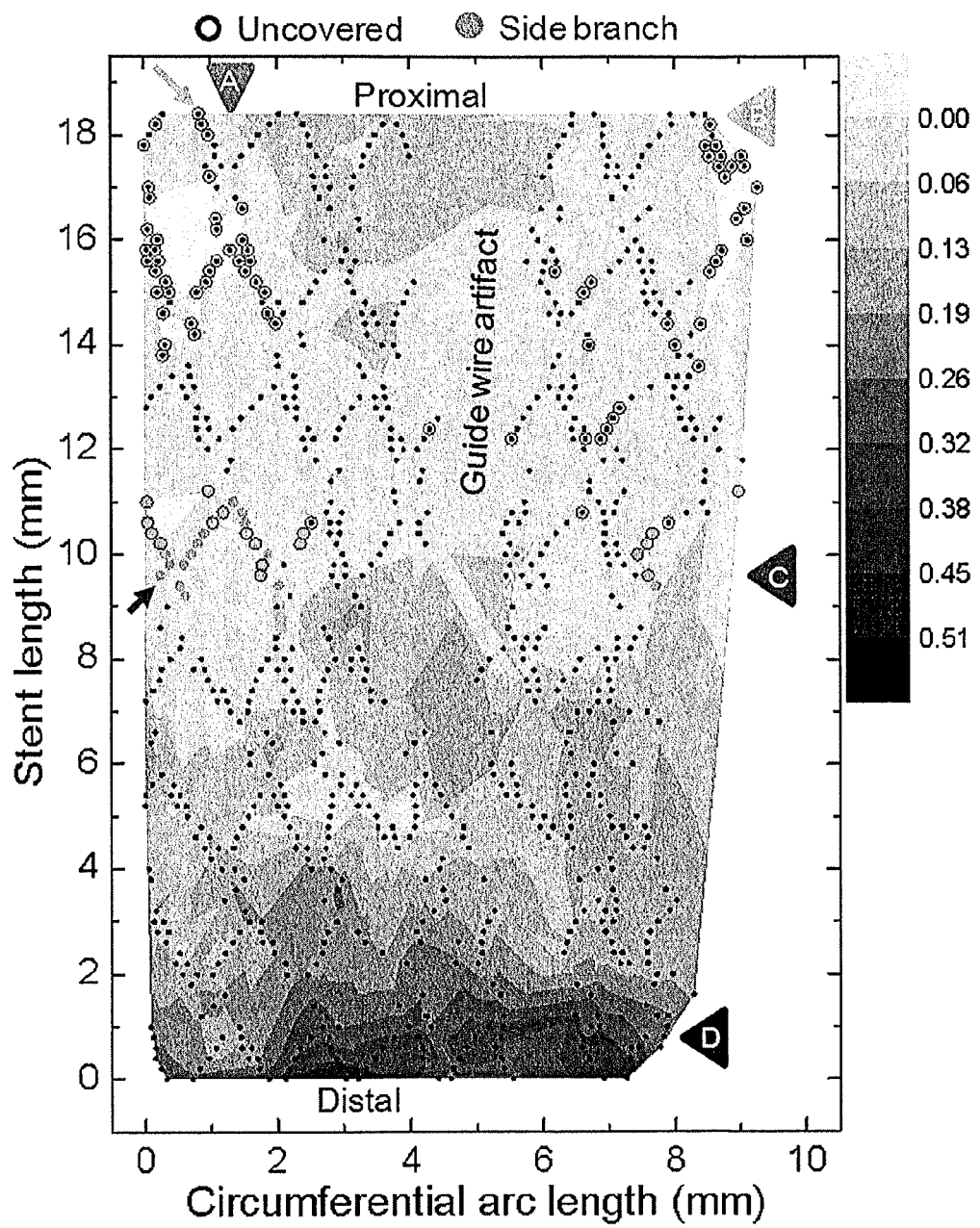
FIG. 8 is a diagram showing an image composited at a composition unit according to one exemplary embodiment of the present invention.

FIG. 8 is a diagram showing an image used to analyze a blood vessel into which a stent is inserted, as generated according to one exemplary embodiment as shown in FIG. 2. The x axis (i.e., horizontal axis) of an image means a length a blood vessel in a circumferential direction from a strut control point, and the y axis (i.e., longitudinal axis) of an image means a length of a blood vessel in a longitudinal direction from a terminal portion of the stent. The color index table at the right side of FIG. 8 refers to a thickness of a neointima on the contour map, and the upper circles are used to express a state of strut stenosis.

Figure 3:
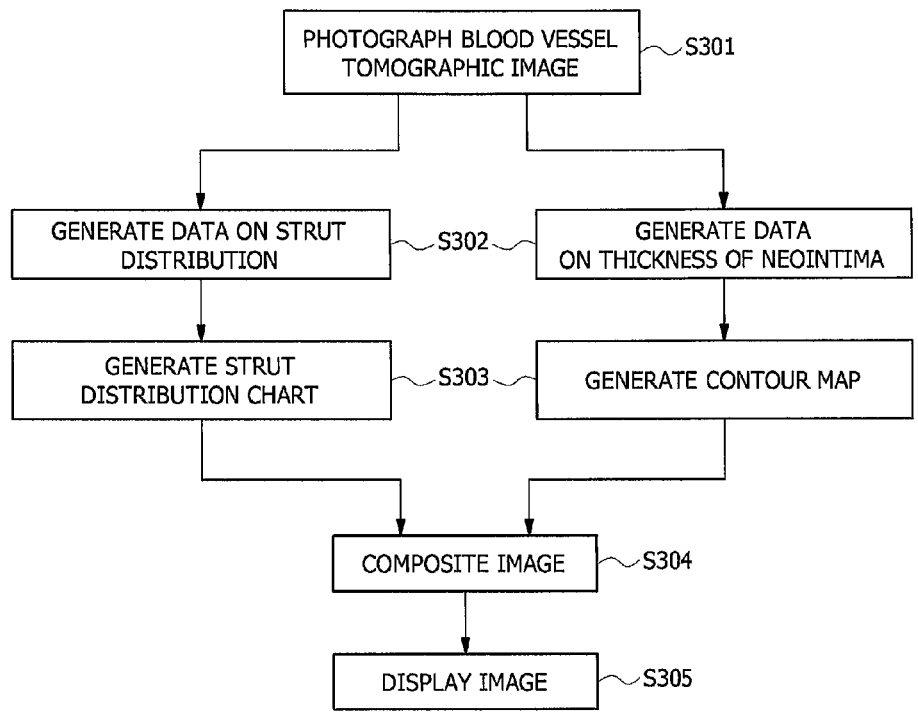
FIG. 3 is a flowchart of a method of providing an image according to still another exemplary embodiment of the present invention.

FIG. 3 is a flowchart of a method of providing an image to analyze a blood vessel according to still another exemplary embodiment of the present invention. The method of providing an image to analyze a blood vessel according to still another exemplary embodiment of the present invention includes photographing a plurality of tomographic images of a tissue in a blood vessel into which a stent is inserted at the imaging unit 10, analyzing the plurality of tomographic images to generate data on strut distribution of the stent at the first analysis unit 21, analyzing the plurality of tomographic images to generate data on a thickness of a neointima at the second analysis unit 22, generating a strut distribution chart of a 2D image at the first image generation unit 31 using the data on strut distribution, generating a contour map for the thickness of the neointima at the second image generation unit 32 using the data on the thickness of the neointima, compositing the strut distribution chart and the contour map at the composition unit 40, and externally displaying the image composited at the composition unit 40 at the display unit 50.

The imaging unit 10 is inserted into a blood vessel into which the stent is inserted to photograph tomographic images in the blood vessel while moving in a longitudinal direction of the blood vessel. The imaging unit 10 may photograph tomographic images in the blood vessel at intervals of 0.01 to 1 mm in a longitudinal direction of the blood vessel. In this case, the plurality of photographed tomographic images are transferred to the first analysis unit 21 and the second analysis unit 22 (S301).

The first analysis unit 21 analyzes the plurality of tomographic images photographed at the imaging unit 10 to generate data on strut distribution. The first analysis unit 21 may generate the data on strut distribution by measuring a location of strut stenosis in a longitudinal direction of the stent in the blood vessel, and a location of strut stenosis in a circumferential direction of the stent. Here, a method of generating data on strut distribution is as shown in FIG. 1.

The second analysis unit 22 analyzes the plurality of tomographic images photographed at the imaging unit 10 to generate data on a thickness of a neointima. The second analysis unit 22 may generate the data on the thickness of the neointima using a value obtained by subtracting a linear distance running from a vessel wall to the strut from the thickness of the neointima. Here, a method of generating the data on the thickness of the neointima is as shown in FIG. 1.

The generation of data at the first analysis unit 21 and the second analysis unit 22 is not limited to this exemplary embodiment. For example, the second analysis unit 22 may first generate the data on the thickness of the neointima, or may generate the data on the thickness of the neointima at the same time as generation of the data on strut distribution (S302).

The first image generation unit 31 generates a strut distribution chart of a 2D image using the data on strut distribution. The first image generation unit 31 may generate the strut distribution chart by measuring a location of strut stenosis in a longitudinal direction of the stent in the blood vessel, and a location of strut stenosis in a circumferential direction of the stent. For example, a method of generating the strut distribution chart is as shown in FIG. 1.

The second image generation unit 32 generates a contour map for the thickness of the neointima using the data on the thickness of the neointima. The second image generation unit 32 may draw a contour line by connecting points having the same values obtained from the 2D image, and generate the contour map for the thickness of the neointima using the contour line. For example, a method of generating the contour map is as shown in FIG. 1.

The generation of the strut distribution chart and the generation of the contour map are not limited to this exemplary embodiment. For example, the second analysis unit 22 may first generate the contour map, or may generate the contour map at the same time as generation of the strut distribution chart (S303).

The composition unit 40 composites the strut distribution chart and the contour map to generate an image for blood vessel analysis (S304), and the display unit 50 externally displays the image composited at the composition unit 40 on a display device (S305).

The system and method for providing an image according to the present invention can realize conversion of a 3D tissue structure into which an implant is inserted into a 2D image using a contour technique.

Also, the system and method for providing an image according to the present invention can provide an image including information on a location of an implant in a tissue, distribution, a state of stenosis, a progression level of periimplantitis, and a thickness of a neointima.

While the invention has been shown and described with reference to certain exemplary embodiments thereof, it will be understood by those skilled in the art that various changes in form and details may be made therein without departing from the scope of the invention as defined by the appended claims.

What is claimed is:

1. A system for providing an image, comprising: an imaging unit configured to photograph an inner part of a blood vessel into which a stent is inserted to provide a plurality of tomographic images;
   a first analysis unit configured to analyze the plurality of tomographic images to generate data on strut distribution of the stent;
   a second analysis unit configured to analyze the plurality of tomographic images to generate data on a thickness of a neointima;
   a first image generation unit configured to generate a strut distribution chart of a 2D image using the data on the strut distribution;
   a second image generation unit configured to generate a contour map for the thickness of the neointima using the data on the thickness of the neointima; and
   a composition unit configured to composite the strut distribution chart and the contour map,
   wherein the second analysis unit generates the thickness of the neointima using a linear distance running from the strut to a newly formed vessel wall when the strut is stenosed in a preexisting vessel wall, or generates the thickness of the neointima subtracting a linear distance running from the preexisting vessel wall to the strut from a linear distance running from the strut to the newly formed vessel wall when the strut is not stenosed in the preexisting vessel wall, or generates the thickness of the neointima as zero (0) when the strut is stenosed in the preexisting vessel wall but the neointima is not generated, or generates the thickness of the neointima using a negative number having a size corresponding to a linear distance running from the preexisting vessel wall to the strut,
   wherein the second image generation unit draws a contour line by connecting points having the same values obtained from the data of the thickness of the neointima generated at the second analysis unit and generates a contour map using the contour line, and
   wherein the composition unit displays the contour map in a different shade depending on the contour line generated using the thickness of the neointima.

2. The system of claim 1, wherein the first analysis unit is configured to generate the data on the strut distribution by measuring a strut location of the stent in a blood vessel in a longitudinal direction and a strut location of the stent in a circumferential direction.

3. The system of claim 2, wherein the first analysis unit is configured to measure a strut location of the stent in a longitudinal direction with respect to a terminal portion of the stent, and measure a strut location of the stent in a circumferential direction with respect to a strut control point colliding with a baseline extending from a centrifugal point of the stent.

4. The system of claim 3, wherein the first image generation unit is configured to generate the strut distribution chart using the x axis of the 2D image as the strut location of the stent in a circumferential direction and the y axis of the 2D image as the strut location of the stent in a longitudinal direction.

5. The system of claim 1, further comprising:
a third analysis unit configured to analyze the plurality of tomographic images and generate data on strut stenosis according to a state of stenosis of the strut in the blood vessel,
wherein the first image generation unit is configured to discriminatively display struts on the strut distribution chart according to the data on the strut stenosis.

6. The system of claim 5, wherein the data on the strut stenosis comprises information on the presence of stenosis of the implant in the blood vessel and location relationship between the neointima and the implant.

7. The system of claim 6, wherein the information on the location relationship between the neointima and the strut is classified into one of a case in which the strut is stenozed in the vessel wall and surrounded by the neointima (covered), a case in which the strut is stenozed in the vessel wall but is not surrounded by the neointima (uncovered), and a case in which the strut is not stenozed in the tissue (malapposed).

8. The system of claim 1, further comprising:
a display unit configured to externally display the image composited at the composition unit.

9. The system of claim 8, wherein the display unit is configured to externally display a tomographic image comprising struts on the image composited at the composition unit.

10. The system of claim 9, wherein the display unit is configured to discernibly display the struts on the tomographic image.

* * * * *